United States Patent [19]

Sacks

[11] 4,331,155
[45] May 25, 1982

[54] DIGITAL CUFF APPARATUS FOR DETERMINING BLOOD PRESSURE WITHOUT USE OF A STETHOSCOPE

[76] Inventor: Alvin H. Sacks, 12682 Roble Veneno, Los Altos Hills, Calif. 94022

[21] Appl. No.: 109,051

[22] Filed: Jan. 2, 1980

Related U.S. Application Data

[63] Continuation-in-part of Ser. No. 841,241, Oct. 11, 1977, Pat. No. 4,202,347, which is a continuation-in-part of Ser. No. 750,077, Dec. 13, 1976, abandoned, which is a continuation of Ser. No. 584,102, Jun. 5, 1975, abandoned.

[51] Int. Cl.³ ............................................. A61B 5/02
[52] U.S. Cl. ................................................. 128/686
[58] Field of Search ............... 128/672, 674, 677, 678, 128/684, 686, 679–683, 685, 687, 691, 694

[56] References Cited

U.S. PATENT DOCUMENTS

| | | | |
|---|---|---|---|
| 598,343 | 2/1898 | Hill et al. | 128/672 |
| 2,753,863 | 7/1956 | Bailey | 128/680 |
| 3,416,516 | 12/1968 | Cohen et al. | 128/686 |
| 3,585,987 | 6/1971 | Svensson | 128/672 |
| 4,202,347 | 5/1980 | Sacks | 128/686 |

Primary Examiner—William E. Kamm
Attorney, Agent, or Firm—Julian Caplan

[57] ABSTRACT

A cuff having a casing and an inflatable diaphragm is slipped over a portion of the body of the user, preferably a thumb or finger. The diaphragm is connected by a conduit to a pressure source and to a manometer. A preferred pressure source is as a cylinder similar to that of a syringe. A plunger in the syringe inflates the diaphragm. The pressure in the cuff is slowly increased until the subject first notices a slight localized throbbing sensation within the artery inside the cuff, the pressure corresponding to diastolic blood pressure, and this pressure is read. Use of a transducer or even a stethoscope is unnecessary. Further, it has been found that if the cuff is properly designed, pressure corresponds very closely to diastolic blood pressure measured at the brachial artery with a standard arm cuff using a stethoscope. For other cuff structures the pressure in the cuff may be calibrated to that in an arm by using these subjective sensations. The pressure is increased further until the subject senses the disappearance of the localized throbbing within the artery, a condition which corresponds to systolic blood pressure, such pressure again being noted.

15 Claims, 6 Drawing Figures

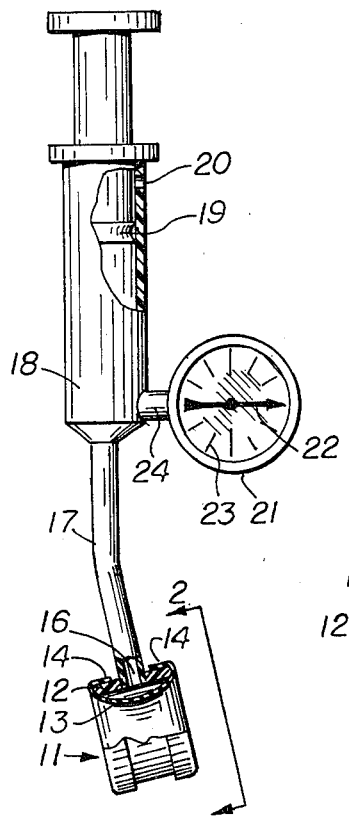
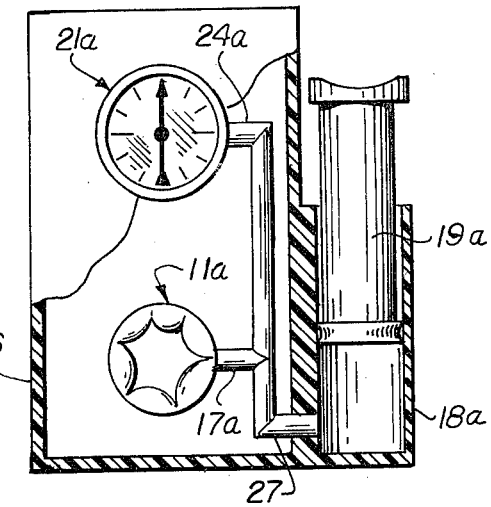
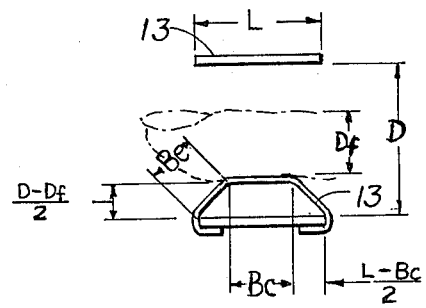
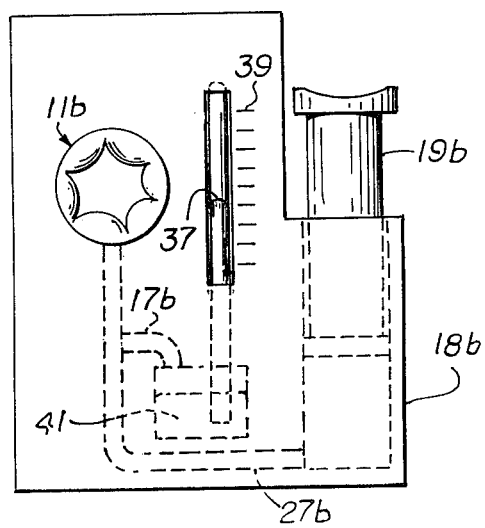
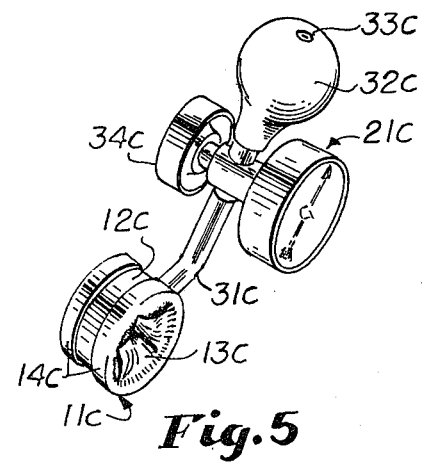

DIGITAL CUFF APPARATUS FOR DETERMINING BLOOD PRESSURE WITHOUT USE OF A STETHOSCOPE

This application is a continuation-in-part of application Ser No. 841,241, filed Oct. 11, 1977, now U.S. Pat. No. 4,202,347, which was a continuation-in-part of application Ser. No. 750,077, filed Dec. 13, 1976, which was, in turn, a continuation of application Ser. No. 584,102, filed June 5, 1975, the latter two applications having been abandoned.

This invention relates to a new and improved digital cuff apparatus for determining blood pressure without use of a stethoscope. More particularly, the invention relates to a cuff which may be placed around a finger, thumb, wrist, or other extremity of the body containing an artery and inflated to perform a function analogous to that of the standard cuff used with a sphygmomanometer. The cuff, for example, is inflated either by means of a squeeze bulb or by a cylinder having a plunger resembling a syringe. By proper proportioning of the dimensions of the cuff, the cuff pressure measured at onset and cessation of the Korotkoff sensations are found to correspond to the systolic and diastolic blood pressures measured at the brachial artery.

It has been found by the inventor that with very little practice or training the average person can sense in the finger, wrist or arm the onset and cessation of conditions which are ordinarily detected by auscultation, conventionally by use of a stethoscope, to determine both systolic and diastolic readings of blood pressure.

By using the cuff and structure herein described and by eliminating the use of a transducer or even a stethoscope, a simplified device for determining a patient's own blood pressure for home use is thus provided.

Accordingly, a principal purpose of the present invention is to simplify the equipment and procedure required to determine blood pressure. The use of a transducer or a stethoscope is eliminated in that the patient's own sensations in the artery of a finger or other extremity are used to determine the times at which the systolic or diastolic pressure reading is to be taken. Also, the wrap-around cuff is eliminated in favor of a fixed cylindrical cuff which is slipped over a finger or thumb and is designed and calibrated in such a way as to give accurate systolic and diastolic blood pressure readings.

The development of modern blood pressure measurements is attributed primarily to two individuals. The first important advance was in 1896 by Riva Rocci who invented an inflatable penumatic cuff for the upper arm used to obliterate the pulse at the wrist. The second major advance was in 1905 when Korotkoff suggested that the sounds heard with a stethoscope placed over the brachial artery just distal to the cuff should be used as indices of systolic and diastolic pressure. Since 1905, there has been considerable refinement and automation of equipment; but, nevertheless, at the present time, blood pressure is ordinarily determined by a physician or a trained technician employing an inflatable cuff usually attached to the upper arm, and a stethoscope placed over an artery below the cuff. Alternatively, the physician's function is sometimes performed by automated equipment and the stethoscope is replaced by microphone or other transducers. In any case, the cuff is inflated until circulation through the artery is stopped; then the pressure is gradually reduced and the pressure on the manometer noted (or recorded) when the first sound is detected corresponding to the systolic pressure, and then the pressure reading on the manometer is noted when the last sound disappears (or fades) corresponding to diastolic pressure.

As has previously been mentioned, the present invention is based on a new concept, namely, that the subject can sense arterial sensations of the phenomenon of his blood flow and artery behavior which is responsible for producing the Korotkoff sounds. Hence, the need for a stethoscope or a transducer is eliminated, and the subject merely measures the points and the range of pressures at which the localized sensations in the artery begin and subside as applied pressure is increased or reduced.

Shortly before Korotkoff's discovery, Gertner, in 1899, introduced a thumb cuff combined with a mercury manometer which was to be used to measure blood pressure by first blanching the finger or thumb by immersion into a special cup while inflating the cuff, then gradually lowering the cuff pressure and observing the pressure on the manometer at which the sudden flush of color returned to the finger tip (the so-called "flush" technique). This technique gives only systolic pressure. The length/diameter ratio of Gartner's cuff was 0.4.

The experimental data of Menlowitz in 1938 and of Weaver and Bohr in 1950 both indicate that there is a "brachial-digital gradient" showing that systolic blood pressure measurements in the digits are substantially lower than the blood pressures measured at the brachial artery, in amounts of the order of 20 mmHg. However, these data were obtained with a wrap-around thumb cuff measuring 4 cm. in width, which amounts to a length/diameter ratio of the cuff of approximately 2:1. Gartner used a length/diameter ratio of 0.4, but had no brachial pressures for comparison. It has since been found that the dimensions of the cuff have a substantial effect on the indirect reading of blood pressures as measured at the brachial artery, and this effect was studied by Geddes in 1970. According to the correction curves presented by Geddes, a cuff of the proportions used by Weaver and Bohr would give approximately 12 mm. error in the systolic blood pressure readings. If this correction is applied to the readings obtained by Weaver and Bohr, it is found that the mean difference between brachial and digital systolic blood pressure is only 6.7 mmHg. It is apparent that the so-called "digital-brachial gradient" depends strongly upon the cuff design used in the digital cuff and that an appropriate cuff design can be made which will minimize this difference. Furthermore, the use of a wrap-around cuff insures that a smaller finger with the same cuff will yield an even higher value of length to diameter and thus yield even larger errors in the digital blood pressure. On the other hand, if one uses a rigid slip-on cuff as described herein, there are compensating errors for small fingers. In particular, for a smaller finger, the length/diameter ratio increases, producing lower pressure readings; but, on the other hand, the ratio of the cuff diameter to finger diameter is increased, thus producing higher pressure readings and compensating the former effect. The reason for the higher readings with a larger diameter ratio of cuff to finger was recognized long ago and is associated with the higher cuff pressure required to transmit pressures to the digit in question. According to the correction curves presented by Geddes for cuff length/diameter ratio, one finds that a length to diameter ratio of about 1.4 should yield a correction of zero of the systolic pressure (only systolic pressures were measured by Weaver and Bohr, as well as by Gertner, because of the limitations of their technique). It has been found, in accordance with the present invention, that the so-called brachial-digital gradient depends largely on the cuff design used at the thumb and appears to be quite consistent. Therefore, one has two possible design choices to eliminate the so-called gradient, which appears to be an artifact rather than physiologic fact. The choices are: (a) to select a thumb cuff design to minimize the brachial differential; or (b) to recalibrate the pressure scale for any given thumb cuff design so as to force agreement with measurements at the brachial artery. It is possible to obtain arterial blood pressure readings for both systolic and diastolic pressures by using the method and apparatus described herein and applying the apparatus to a thumb or finger of the subject.

The readings of blood pressure obtained by indirect measurements (i.e., by measurement from outside the body) are known to depend upon the design of the pneumatic cuff. In particular, it is known that a very wide cuff produces artificially low blood pressure readings, whereas a very narrow cuff produces artificially high blood pressure readings. For this reason, a "standard" cuff width is now prescribed in order to "standardize" blood pressure readings. Ordinarily, this width is prescribed in relation to the circumference of the arm being monitored. Thus, wider cuffs are to be used for obese persons.

The medical literature has indicated that the pressures in the thumb or fingers obtained by indirect measurement are generally lower than those obtained in the upper arm, but these findings are based on measurements made by employing two different measurement techniques at the two locations, namely, the Korotkoff technique at the upper arm and the so-called "flush" technique at the thumb. The latter refers to observing the cuff pressure at which the color suddenly returns to the blanched finger as the cuff pressure is lowered. Blanching is accomplished either with a tourniquet or by raising the finger above heart level while the cuff is inflated. The flush technique yields a value only for systolic blood pressure. The reason for using this approach for digital pressures lies primarily in the difficulty in detecting Korotkoff sounds at the thumb.

Applicant has discovered that:

(a) Using his technique employing specific localized subjective sensations permits the use of the same technique both at the finger or thumb and at the forearm.

(b) Indirect blood pressures measured by this technique at the upper arm agree very closely with measurements using a stethoscope.

(c) Indirect blood pressure measured by this technique at the thumb closely follow those made at the upper arm, (d) Any consistent difference can be eliminated either by proper cuff design for the thumb or, alternatively, by a one-time recalibration of the pressure gauge used with the thumb cuff.

On the basis of these observations, the inventor has found that indirect systolic and diastolic blood pressures can be accurately measured at the thumb or finger using the concepts and designs hereinafter set forth.

The proportions of the thumb cuff in terms of length-/diameter ratio can be determined by a series of tests comparing thumb versus arm pressures and other test series in which the thumb cuff dimensions are varied and thumb cuff readings compared with one another. It will be understood that there may be many combinations of cuff dimension, length/diameter ratio, overlap and elasticity which can be made to work by using the principles described herein. Applicant has performed numerous tests and developed several useable designs. On the other hand, within certain limits, if any specific thumb cuff design is selected, then the pressure gauge indicating thumb pressures can simply be recalibrated to account for any digital-brachial pressure gradient observed using that cuff. For some cuff designs, however, the latter approach might lead to an unacceptable variation of indicated blood pressure readings with finger size. Thus, by either using proper thumb cuff proportions or by calibrating pressure gauge for selected cuff design, it is possible to obtain accurate systolic and diastolic blood pressure readings on the thumb or fingers using applicant's methods and apparatus.

By the use of the engineering technique known as dimensional analysis, it can be shown that the ratio of indicated blood pressure to true blood pressure is a function of three dimensionless ratios, namely, the ratio of finger diameter ($D$) to cuff diameter ($D$), the ratio of cuff length ($L$) to diameter of the cuff, and finally, the ratio of the length of the flexible bladder ($B$) inside the cuff to the diameter of the finger, but the latter ratio can be expressed mathematically in terms of the former two, if we stipulate that the length of the flexible bladder is just sufficient to provide a length of contact with the finger which agrees with the optimum length of contact for a given diameter digit which will insure the closest agreement between indirect and direct blood pressure readings. Thus, according to the most recent work of Geddes (1978), the optimum ratio of bladder contact length to finger diameter (i.e., $B_c/D_f$) is approximately 1.25. If we then assume that the longitudinal cross sectional shape of the inflated bladder consists of two triangles and a rectangle, such as to insure this length of contact (see FIG. 6), then we may write the following mathematical relationships:

$$\frac{B_c}{D_f} = \frac{1}{.8} = 1.25 \text{ (Geddes)}$$

$$B^2 = \left[\frac{L - B_c}{2}\right]^2 + \left[\frac{D - D_f}{2}\right]^2$$

$$\frac{B}{D_f} = \frac{2B_e + B_c}{D_f} = \frac{2B_e}{D_f} + \frac{B_c}{D_f} = 1.25 + 2 \cdot$$

$$\sqrt{\frac{\left[\frac{L - B_c}{2}\right]^2 + \left[\frac{D - D_f}{2}\right]^2}{D_f^2}}$$

Thus, we find that the ratio:

$$\frac{B}{D_f} = 1.25 + \sqrt{\left[\frac{L}{D_f} - 1.25\right]^2 + \left[\frac{D}{D_f} - 1\right]^2}$$

Using this relationship, we can select values of $D_f/D$ and $L/D$ and calculate the optimum ratio $B/D_f$. Carrying out these calculations leads to the following table.

| $\frac{L}{D}$ | $\frac{D_f}{D}$ | $\frac{L}{D_f}$ | $\left[\frac{D}{D_f}-1\right]^2$ | $\left[\frac{L}{D_f}-1.25\right]^2$ | $\frac{B}{D_f}$ | $\frac{B}{L}$ |
|---|---|---|---|---|---|---|
| .8 | .8 | 1.0 | .0625 | .0625 | 1.60 | 1.60 |
|  | .6 | 1.33 | .444 | .0064 | 1.92 | 1.44 |
|  | .4 | 2.0 | 2.25 | .5625 | 2.93 | 1.47 |
| 1.0 | .8 | 1.25 | .0625 | 0 | 1.50 | 1.20 |
|  | .6 | 1.67 | .444 | .176 | 2.04 | 1.22 |
|  | .4 | 2.5 | 2.25 | 1.56 | 3.20 | 1.28 |
| 1.2 | .8 | 1.5 | .0625 | .0625 | 1.60 | 1.07 |
|  | .6 | 2.0 | .444 | .5625 | 2.25 | 1.13 |
|  | .4 | 3.0 | 2.25 | 3.0625 | 3.55 | 1.18 |

The inventor has carried out numerous experimental tests using various cuff dimensions and has selected empirically (on the basis of measured blood pressure) a cuff whose dimensions were later found to agree extremely well with one of the cases shown above. Specifically, the dimensions of the cuff arrived at experimentally are as follows: L=1 inch, D=1 inch, B=1.2 inch. As was found experimentally, it can be seen from the above table that the variation of the optimum length, B, is minimal over a wide range of finger sizes. It will be understood, that small variations of these combinations of parameters may also give acceptable blood pressure readings. In any event, for any selected cuff dimensions, one can "calibrate" the system experimentally and thus force the pressure gauge readings to agree with blood pressures measured at the brachial artery with the standard technique. However, if the cuff design varies substantially from the optimum design, there is the strong possibility that such a calibration will be useful for only a small range of finger sizes. In fact, if B/L is excessively large, then the bladder inflates outside the cuff where pressure is not effectively transmitted to the artery. Calibration of such a cuff may not even be possible. If the bladder is elastic, this problem is aggravated, as the inventor has found experimentally, since increased cuff pressure will at some point simply stretch the bladder at the ends of the cuff without communicating increased pressure to the finger.

The object of applicant's method and apparatus for measuring blood pressure is to simplify both apparatus and the procedure for measuring blood pressure and to make them easily applicable to measuring one's own blood pressure.

Thus, the advantages of applicant's invention include:
1. The need for a stethoscope or transducer is eliminated.
2. Listening is not required, so the subject may be totally deaf.
3. Need for applying an arm cuff or for adjusting or removing clothing is eliminated.
4. No assembly of parts or components is required of the user.
5. No need to blanch the finger or thumb as in the flush technique.

The device of the invention thus comprises a cuff which encircles a portion of the subject's body containing an artery, the cuff including a casing and a diaphragm inside the casing to engage the body portion, the diaphragm being inflatable against the body portion to effect in the subject a localized throbbing sensation in the artery. The casing and diaphragm define two of the walls of the chamber which confine a fluid to inflate the diaphragm, and a control means cooperable with the chamber so as to vary the fluid pressure therein. In cooperation with the control means is an indicator means which indicates highest and lowest pressures at which the subject feels a localized throbbing sensation in the artery, the indicator means thereby providing indications of diastolic and systolic blood pressure. The indicator means include: a scale calibrated to indicate blood pressure corresponding to brachial blood pressures measured by the standard auscultatory technique.

Other objects of the present invention will become apparent upon reading the following specification and referring to the accompanying drawings in which similar characters of reference represent corresponding parts in each of the several views.

In the drawings:

FIG. 1 is a schematic elevational view of one embodiment of the present invention partially broken away in section to reveal internal construction.

FIG. 2 is an enlarged view taken substantially along the line 2—2 of FIG. 1 showing a cuff construction, it being understood that essentially the same cuff construction is used in all the modifications herein illustrated.

FIG. 3 is a front elevational view partly broken away in section of another embodiment of the invention.

FIG. 4 is a view similar to FIG. 3 of still another embodiment of the invention.

FIG. 5 is a perspective view showing a fourth embodiment of the present invention.

FIG. 6 is a schematic diagram for dimensional analysis.

Directing attention first to the embodiments of FIGS. 1 and 2, a cuff 11, preferably dimensioned as heretofore explained, is provided comprising a cylindrical, rigid casing 12. In the interior thereof is a tubular diaphragm 13, the ends 14 of which are preferably brought around the outside of casing 12 and secured thereto by cement, bands (now shown) or other means. The relaxed diaphragm 13 is sufficiently large to conveniently fit over the finger or thumb of the user. Opening 16 is formed in casing 12 on the outside of diaphragm 13 and is connected by a duct to tube 17 fixed to the end of cylinder 18 of a type conventionally used in syringes for injections. Fitting in fluid-tight relation to the internal wall of cylinder 18 is a plunger 19 of any conventional type. Communicating with the pressurized end of cylinder 18 is a manometer 21 here being of an aneroid type having a pointer 22 which reads pressure in conjunction with a scale 23. The pressurized manometer 21 is connected to the pressurized end of cylinder 18 by means of duct 24.

In use of the device shown in FIGS. 1 and 2, the diaphragm 13 is relaxed. Cuff 11 is slipped over the thumb. Plunger 19 is inserted in the cylinder 18 (if it has not already been so inserted), air escaping through vent 20 until the end of the plunger closes off the vent 20. Plunger 19 is moved slowly into the cylinder 18, causing the diaphragm 13 to be pressurized and gradually cut off circulation through the digital artery in the finger. At some point during this variable pressurizing of the diaphragm over a range of pressures, the subject can feel a slight localized throbbing sensation in the artery inside the cuff 11 which corresponds to the diastolic blood pressure. When such throbbing sensation is sensed, the reading of pointer 22 on scale 23 is noted. Plunger 19 is further depressed until the subject notes the point in the pressure range at which the localized arterial throbbing stops, which indicates the systolic pressure has been reached, and again the reading of the manometer is noted. Preliminary to use of the device, the markings 23 have been calibrated with a standard sphygmomanometer so that direct readings of blood pressure are obtainable.

It will be understood that a reverse procedure may be followed, namely, the diaphragm 13 is fully pressurized over a range of pressures by depressing plunger 19, the plunger is then slowly withdrawn until the point at which localized arterial throbbing first commences and a reading made of systolic pressure, then the plunger further withdraws until the point at which the localized throbbing sensation ends and a reading made of diastolic pressure.

Directing attention to the structure of FIG. 3, a casing 26 is provided having an opening in which cuff 11a is inserted. Thus, in this form of the invention, the user inserts his thumb or finger into the opening in the diaphragm 13. Connected to or integral with the casing 26 is cylinder 18a into which fits plunger 19a in fluid-tight manner. A duct 27 connects the lower end of cylinder 18a to the duct 17a and also to a duct 24a which connects to a manometer 21a. Operation of the device is essentially the same in this embodiment as in the preceding embodiment.

The embodiment of FIG. 4 resembles that of FIG. 3, except that aneroid manometer 21a is replaced by a mercury manometer 37. Thus, duct 27b connects to air space at the top of mercury bulb 41 from which extends tube 37 which is read with scale 39. Duct 17b interconnects the air space at the top of bulb 41 with cuff 11b.

The device of FIG. 5 is very simple. The cuff 11c is connected by tube 31c to the squeeze bulb 32c having a check valve 33c and a bleed valve 34c. Aneroid manometer 21c is also connected into the system as shown. This device is used in the manner of FIG. 1 or 3.

The elements of FIGS. 3, 4 and 5 are, in many respects, similar to, or identical with, corresponding elements in the preceding embodiments, and the same reference numerals followed by the subscripts a, b and c, respectively, are used to designate corresponding parts.

The term "digit" is used herein to mean a finger, thumb or toe. The term "reading on second manometer the systolic and diastolic brachial arterial pressures" means using standard auscultatory technique.

What is claimed is:

1. A device for determining systolic and diastolic blood pressures comprising an inelastic annular cross-section cuff to encircle a digit, an inflatable tubular diaphragm extending around the entire inside of said cuff inflatable to affect blood flow through said digit, a pressurizing member, duct means communicating from said pressurizing member to the interior of said diaphragm, whereby pressuring said pressurizing member pressurizes said diaphragm to cut off blood flow through said digit, indicator means for reading the gaseous pressure in said pressurizing member at different pressures to determine said pressure at the onset and cessation of Korotkoff phenomena by using subjective localized arterial sensations within the cuff, the ends of said tubular diaphragm being turned back over the ends of said cuff, and seal means at opposite ends of said cuff to form an air-tight seal of said ends of said tubular diaphragm with said cuff, said duct means opening into said cuff intermediate said seal means.

2. A device according to claim 1 in which said pressurizing member is a cylinder having a plunger.

3. A device according to claim 2 which further comprises a casing having wall means, said wall means including said pressurizing member and said indicator means, said cuff and said duct means being contained within said casing.

4. A device according to claim 1 in which said indicator means comprises a manometer.

5. A device according to claim 4 in which said manometer is of the aneroid type.

6. A device according to claim 4 in which said manometer is of the mercury column type.

7. A device according to claim 4 in which the manometer has pressure scale markings, said markings being calibrated corresponding to standard brachial blood pressure readings.

8. A device according to claim 1 in which the proportion of the length of said cuff to the inside diameter of said diaphragm is in a first ratio between 0.8 and 1.2 and the proportion of the length of said diaphragm to the length of said cuff is in a second ratio between 1.6 and 1.07.

9. A device according to claim 8 in which said first ratio is about 1:1 and said second ratio is about 1.2:1.

10. A device for determining systolic and diastolic blood pressures of a human subject comprising an inelastic cuff to encircle a digit containing an artery, said cuff including a casing and a diaphragm inside said casing to engage said digit, said diaphragm being inflatable against said digit to affect blood flow in said artery and thus to effect in the subject a localized throbbing sensation in said artery, a chamber to confine gaseous fluid communicating with said diaphragm for inflating said diaphragm, control means cooperable with said chamber to vary the pressure in said chamber thereby varying the pressure against said diaphragm, indicator means cooperable with said control means to indicate pressure in said chamber at the highest and lowest pressures at which the subject feels a localized throbbing sensation in said artery, said indicator means thereby providing indications of diastolic and systolic blood pressure at said lowest and highest pressures, respectively.

11. A device for determining systolic and diastolic blood pressures comprising an inelastic, annular cross-section cuff to encircle a digit, an inflatable, annular cross-section diaphragm extending around the entire inside of said cuff inflatable to affect the blood flow through said digit, a pressurizing member, duct means communicating from said pressurizing member to the interior of said diaphragm, whereby pressuring said pressurizing member pressurizes said diaphragm to cut off blood flow through said digit, indicator means for reading the gaseous pressure in said pressurizing member at different pressures to determine said pressure at the onset and cessation of Korotkoff phenomena by using subjective localized arterial sensations within the cuff, the proportion of the length of said cuff to the inside diameter of said diaphragm being in a first ratio between 0.8 and 1.2 and the proportion of the length of said diaphragm to the length of said cuff being in a second ratio between 1.6 and 1.07.

12. A method of determining systolic and diastolic blood pressures of a human subject without use of a stethoscope or transducer by the use of an apparatus comprising an inelastic cuff shaped to encircle a portion of the subject's body containing an artery and having a diaphragm on the inside of said cuff inflatable to affect blood flow through said artery, first means to inflate and pressurize said diaphragm, and manometer to indicate pressure in said diaphragm and said first means, said method comprising:
- a first step of applying said cuff around said portion,
- a second step of actuating said first means until the subject feels a localized throbbing sensation in the artery within said cuff,
- a third step of making a first reading of said manometer to read the pressure in said first means and the pressure in said diaphragm, said first reading indicating diastolic blood pressure of the subject,
- a fourth step of still further actuating said first means until the throbbing sensation within said artery inside said cuff terminates, and
- a fifth step of making a second reading of said manometer to read the pressure in said first means, said second reading indicating systolic blood pressure of the subject, said first means comprising a syringe-like device having a cylinder having a first and a second end and a plunger movable within the second end of said cylinder, said first end being connected to said diaphragm, and in which said second step comprises moving said plunger inward of said cylinder, and said fourth step comprises moving said plunger inward of said cylinder a greater distance than said second step.

13. A method for determining systolic and diastolic blood pressure of a human subject without use of a stethoscope or transducer comprising the steps of applying an inflatable diaphragm enclosed in an inelastic cuff over a portion of the body of the subject containing an artery, variably pressurizing said diaphragm over a range of pressures in which the subject feels a localized throbbing sensation in said artery within said cuff, determining by means of a manometer when the pressures in said diaphragm are at the higher and lower ends of said range by the subject's sensing in said body portion the presence of said throbbing sensation just at each end of said range and the absence of said throbbing sensation just outside of each end of said range, and measuring by means of a manometer the pressures in said diaphragm at both ends of said range, the pressure measured at said lower end providing a measure of the diastolic blood pressure of the subject and the pressure measured at said upper end providing a measure of the systolic blood pressure of the subject, said step of variably pressurizing said diaphragm comprising providing a cylinder connected to said diaphragm and a plunger in said cylinder and moving said plunger in said cylinder.

14. A method for determining systolic and diastolic blood pressure of a human subject without use of a stethoscope or transducer comprising the steps of applying an inflatable diaphragm enclosed in an inelastic cuff over a portion of the body of the subject containing an artery, variably pressurizing said diaphragm over a range of pressures in which the subject feels a localized throbbing sensation in said artery within said cuff, determining by means of a manometer when the pressures in said diaphragm are at the higher and lower ends of said range by the subject's sensing in said body portion the presence of said throbbing sensation just at each end of said range and the absence of said throbbing sensation just outside of each end of said range, and measuring by means of a manometer the pressures in said diaphragm at both ends of said range, the pressure measured at said lower end providing a measure of the diastolic blood pressure of the subject and the pressure measured at said upper end providing a measure of the systolic blood pressure of the subject, said step of variably pressurizing said diaphragm comprising providing a squeeze bulb and a tube connected to said diaphragm and squeezing said tube to force air into said tube.

15. A device for determining systolic and diastolic blood pressures without the use of a stethoscope or transducer comprising an inelastic cuff to fully encircle a digit of the subject, an inflatable diaphragm on the inside of said cuff inflatable to affect blood flow through said digit, a pressurizing member, duct means communicating from said pressurizing member to the interior of said diaphragm, whereby pressurizing said pressurizing member pressurizes said diaphragm to cut off blood flow through said digit, indicator means for reading the gaseous pressure in said pressurizing member at different pressures to be used for determining said pressure at the onset and cessation of Korotkoff phenomena by using subjective localized arterial sensations within the cuff, said indicator means having a scale which is calibrated corresponding to standard brachial blood pressure readings.

* * * * *